US00PP27259P2

(12) United States Plant Patent
Hurd

(10) Patent No.: US PP27,259 P2
(45) Date of Patent: Oct. 11, 2016

(54) ***LEUCANTHEMUM* PLANT NAMED 'WHOOPS-A-DAISY'**

(50) Latin Name: ***Leucanthemum×superbum* (L. Burbank)**
Varietal Denomination: Whoops-a-Daisy

(71) Applicant: Kevin A. Hurd, Austin, TX (US)

(72) Inventor: Kevin A. Hurd, Austin, TX (US)

(73) Assignee: Walters Gardens Inc, Zeeland, MI (US)

( * ) Notice: Subject to any disclaimer, the term of this patent is extended or adjusted under 35 U.S.C. 154(b) by 174 days.

(21) Appl. No.: 14/121,173

(22) Filed: Aug. 8, 2014

(51) Int. Cl.
*A01H 5/02* (2006.01)

(52) U.S. Cl.
USPC ..... Plt./285

(58) Field of Classification Search
USPC ..... Plt./285
See application file for complete search history.

*Primary Examiner* — Keith Robinson

(57) ABSTRACT

The new Shasta daisy plant, *Leucanthemum* 'Whoops-a-Daisy', is a sturdy plant with dark green serrated foliage and strong heavily-branched stems. The numerous inflorescences have ray tepals of near white developing to pale cream and cover the plant in a mound from the top of the plant to the ground. The new plant is useful in the landscape as a long-flowering border, in mass, as accent plants and containerized for patio or indoor use, or as a cut flower.

1 Drawing Sheet

Botanical classification: *Leucanthemum×superbum* (L. Burbank).

Variety denomination: 'Whoops-a-Daisy'.

BACKGROUND OF THE INVENTION

The original *Leucanthemum×superbum*, or Shasta daisies, were bred by Luther Burbank in the late 1800's as a cross between *Leucanthemum maximum* (Ramond) DC. with *Leucanthemum lacustre* (Broth.) Samp. The new plant, *Leucanthemum* 'Whoops-a-Daisy' originated from a planned breeding program of the inventor, Kevin A. Hurd, at a wholesale perennial nursery in Zeeland, Mich., USA in the summer of 2009. The new *Leucanthemum* was a single selected seedling originally given the breeder number 09-25-01 as an open pollination of an unreleased proprietary female parent identified as 07-15-01 (not patented). The specific male parent is unknown. The present invention relates to a new and distinct cultivar of Shasta daisy botanically known as *Leucanthemum×superbum* and hereinafter referred to by the cultivar name 'Whoops-a-Daisy'.

Asexual reproduction of the new cultivar by stem tip cuttings and shoot tip plant tissue culture at the same nursery in Zeeland, Mich. as early as the summer of 2011 has demonstrated that the new cultivar reproduces true to type with all of the characteristics of the original plant retained through successive generations of asexual propagation.

BRIEF SUMMARY OF THE INVENTION

The new plant, *Leucanthemum* 'Whoops-a-Daisy', is most closely compared to the *Leucanthemum* 'Sonnenschein' (not patented) in flower and *Leucanthemum* 'Snowcap' (not patented) in habit. In test trials in Zeeland, Mich. *Leucanthemum* 'Whoops-a-Daisy' had a shorter, fuller, more compact, rounded habit in flower due to more numerous axillary branching than 'Sonnenschein'. 'Whoops-a-Daisy' also has smaller diameter inflorescence than 'Sonnenschein' with ray tepals that are not as white as 'Sonnenschein'.

Compared to the female parent and grandparent, 'Leukal 01' U.S. Plant Pat. No. 15,204, the new plant has single, lighter colored ray tepals rather fringed, light-yellow, anemone-type flowers. 'Whoops-a-Daisy' is also shorter and more compact than either the female parent or 'Leukal 01'. Other Shasta daisies similar in height include 'Snowcap' which is not as rounded or mounded in habit and has whiter ray tepals than 'Whoops-a-Daisy'.

*Leucanthemum* 'Whoops-a-Daisy' differs from all cultivars known to the inventor in the following combined traits:

1. Sturdy plants with dark green serrated foliage and strongly branched stems.
2. Mounded habit with flowering from the top of the plant to the ground.
3. Flowering with numerous axillary heads.
4. Double row of ray tepals beginning near white and developing to pale cream.

Table one below shows comparisons of other cultivars of *Leucanthemum*.

TABLE 1

| CULTIVAR | HABIT | HEIGHT | COLOR RAY FLORET |
|---|---|---|---|
| Seedling of 'Wirral Pride' × 'Mount Everest' U.S. Plant Pat. No. 1084 | upright | 76 cm | white |
| sport of 'Esther Read' U.S. 1,125 | upright | 90 cm | white |
| 'Barbara Bush' U.S. Plant Pat. No. 9,292 | upright | 75 cm | white |
| 'Sunny Side Up' U.S. Plant Pat. No. 12,837 | upright | 50 cm | white |
| 'Sunny Side Up' U.S. Plant Pat. No. 12,837 | upright | 50 cm | white |
| 'Kiemar' U.S. Plant Pat. No. .12,978 | upright | 19 cm | white |
| 'Angel' U.S. Plant Pat. No. 14,289 | upright | 17 cm | white |
| 'Leukal 01' U.S. Plant Pat. No. 15,204 | upright | 44 cm | light yellow |

TABLE 1-continued

| | | | |
|---|---|---|---|
| 'Kiedal' U.S. Plant Pat. No. 15,636 | upright | 26 cm | white |
| 'Leumayel' U.S. Plant Pat. No. 19,242 | upright | 45 cm | light yellow |
| 'Sante' U.S. Plant Pat. No. 19,829 | upright | 45 cm | light chartreuse |
| 'Daisy Duke' U.S. Plant Pat. No. 21,914 | upright | 56 cm | white |
| 'Engelina' U.S. Plant Pat. No. 22,595 | upright | 55 cm | white |
| 'Victorian Secret' U.S. Plant Pat. No. 22,654 | upright | 51 cm | white |
| 'LWMWH03-0' U.S. Plant Pat. No. 23,151 | upright | 30 cm | near white |
| 'Banana Cream' U.S. Plant Pat. No. 23,181 | upright | 45 cm | light yellow |
| 'LEUZ0001' U.S. Plant Pat. No. 23,426 | upright | 15 cm | white |
| 'Real Galaxy' U.S. Plant Pat. No. 23,873 | upright | 65 cm | ivory |
| 'Bridal Bouquet' U.S. Plant Pat. No. 24,260 | upright | 25 cm | pale yellow |
| 'Goldfinch' U.S. Plant Pat. No. 24,499 | upright | 40 cm | yellow |
| 'Paladin' U.S. Plant Pat. No. 24,844 | upright | 56 cm | white |
| 'Snowcap' (not patented) | mounded | 35 cm | white |
| 'Sonnenschein' (not patented) | upright | 80 cm | pale yellow |
| Whoops-a-Daisy' (not patented) | low mound | 38 cm | near white |

| CULTIVAR | COLOR DISC FLORET | FLOWER TYPE |
|---|---|---|
| Seedling of 'Wirral Pride' × 'Mount Everest' U.S. Plant Pat. No. 1084 | light yellow | anemone |
| sport of 'Esther Read' U.S. 1,125 | white | anemone |
| 'Barbara Bush' U.S. Plant Pat. No. 9,292 | yellow | single |
| 'Sunny Side Up' U.S. Plant Pat. No. 12,837 | light yellow | semi-anemone |
| 'Sunny Side Up' U.S. Plant Pat. No. 12,837 | yellow | single |
| 'Kiemar' U.S. Plant Pat. No. 12,978 | yellow | single |
| 'Angel' U.S. Plant Pat. No. 14,289 | pale yellow green | anemone |
| 'Leukal 01' U.S. Plant Pat. No. 15,204 | light yellow | fringed anemone |
| 'Kiedal' U.S. Plant Pat. No. 15,636 | light yellow | single |
| 'Leumayel' U.S. Plant Pat. No. 19,242 | light yellow | single |
| 'Sante' U.S. Plant Pat. No. 19,829 | chartreuse | fringed anemone |
| 'Daisy Duke' U.S. Plant Pat. No. 21,914 | yellow | single |
| 'Engelina' U.S. Plant Pat. No. 22,595 | yellow | quilled |
| 'Victorian Secret' U.S. Plant Pat. No. 22,654 | yellow | semi-double |
| 'LWMWH03-0' U.S. Plant Pat. No. 23,151 | yellow | single |
| 'Banana Cream' U.S. Plant Pat. No. 23,181 | yellow | semi-double |
| 'LEUZ0001' U.S. Plant Pat. No. 23,426 | yellow | semi-double |
| 'Real Galaxy' U.S. Plant Pat. No. 23,873 | yellow | fringed semi-double |
| 'Bridal Bouquet' U.S. Plant Pat. No. 24,260 | yellow | semi-double |
| 'Goldfinch' U.S. Plant Pat. No. 24,499 | yellow | semi-double |
| 'Paladin' U.S. Plant Pat. No. 24,844 | yellow | single |

TABLE 1-continued

| | | |
|---|---|---|
| 'Snowcap' (not patented) | yellow | single |
| 'Sonnenschein' (not patented) | yellow | single |
| Whoops-a-Daisy' (not patented) | yellow | single |

BRIEF DESCRIPTION OF THE PHOTOGRAPHS

The photographs of the three-year-old new plant demonstrate the overall appearance and landscape qualities of the new plant, including the unique traits. The colors are as accurate as reasonably possible with color reproductions. Ambient light spectrum, source, direction and temperature may cause the appearance of minor variation in color.

DETAILED BOTANICAL DESCRIPTION

Figure 1:
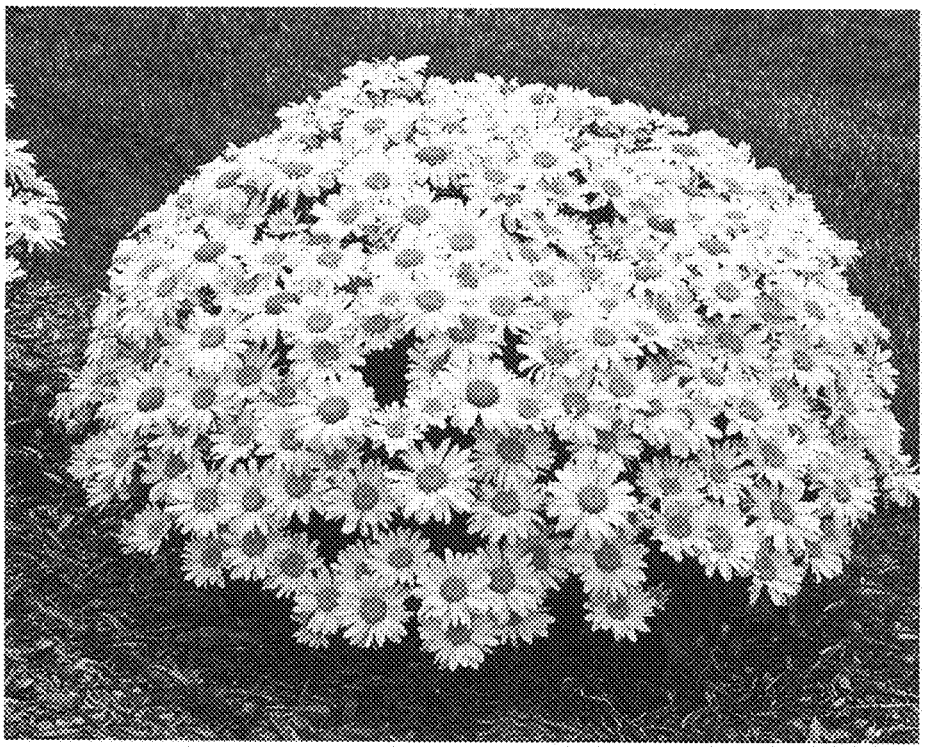
FIG. 1 Shows the new plant at peak flowering with inflorescence covering the plant from nearly top to ground.
Figure 2:
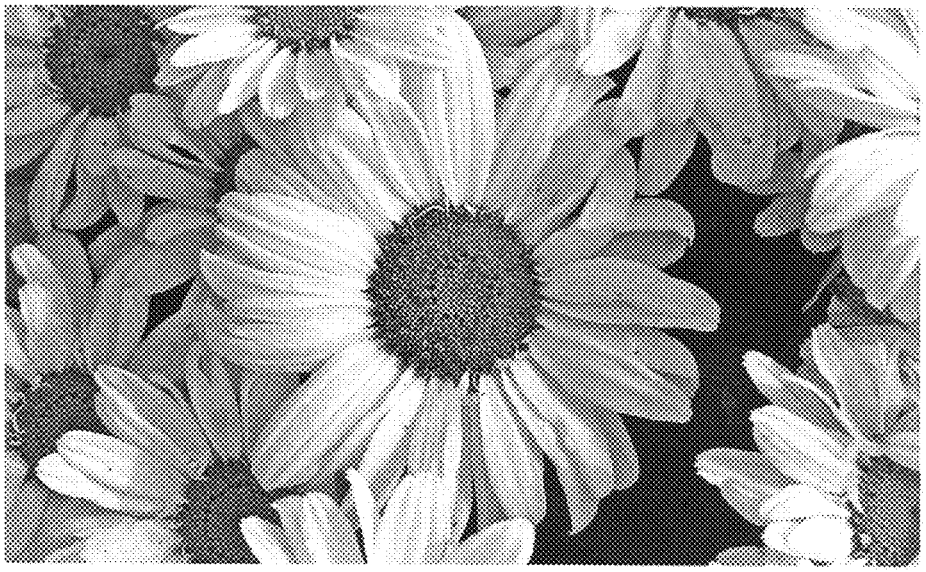
FIG. 2 Shows a close-up of the inflorescence.

The following descriptions and color references are based on the 2001 edition of The Royal Horticultural Society Colour Chart except where common dictionary terms are used. The new plant has not been observed in all possible environments and conditions. The phenotype of *Leucanthemum* 'Whoops-a-Daisy' may vary with different growing conditions such as changes in temperature, light intensity, water availability, fertility, but without change in the genotype.

The plants used for description purposes were two-years old and were grown in Zeeland, Mich. in a full-sun, loamy-sand trial plot environment with supplemental water and limited fertilizer as needed. Summer temperatures range from night lows of about 10° C. to daytime highs of about 34° C. Measurements and numerical values represent averages of trial plants.

Botanical classification: *Leucanthemum×superbum* (L. Burbank).

Parentage: Female parent unreleased proprietary seedling 07-15-01 (not patented); male parent unknown.

Habit: Herbaceous perennial with about eighty branched stems arising from rhizome base; each stem having three to four inflorescences each, rarely two; about 38 cm tall and 64 cm across with rounded top and sides; flowering from top to nearly soil level.

Roots: Fibrous, thin, heavily branched; root color nearest RHS 155D depending on soil type.

Propagation: Tip cuttings or tissue culture; about two weeks to produce young rooted plant; about 33 weeks to finish to flower in 3.8 liter pot depending on season.

Vigor: Excellent, rapid.

Stems: About eighty main stems per plant, strong, upright and angled, 5.0 mm diameter at base, 50 cm tall; canaliculated, hispidulous; about 15 nodes, average internode length about 1.0 cm.

*Stem color*.—Between RHS 139B and RHS 137B.

Axillary branches: Three to four, rarely two per main stem; between 7 to 20 cm long and 4 mm diameter; less canaliculated than main stem, hispidulous; at angles of about 20° from main stem.

*Axillary branch color*.—Between RHS 139B and RHS 137B.

Leaves: Serrated, glabrous above, glabrous below except for main veins hispidulous, dentate with about 16 to 20 teeth per side in lowest leaves and 8 teeth in most distal leaves;

teeth about 1.0 mm long; apex acute; base sessile to attenuate, partially clasping; lowest leaves about 9.0 cm long and 2.0 cm wide, distal leaves 6 cm long and 1 cm wide, average about 7.0 cm long and 1.6 cm wide.

*Leaf color*.—Adaxial color nearest RHS 137A, abaxial color between RHS 137A and RHS 137B; no fragrance detected.

Veins: Major secondary veins anastomosing, adaxial slightly recessed.

*Vein color*.—Abaxial center vein nearest RHS 144A and secondary veins nearest RHS 138A toward base becoming same as surrounding leaf tissue in proximal half; adaxial center vein between RHS N144A and RHS 144A, secondary veins nearest RHS 138B on adaxial side.

Inflorescence: Capitate, about 240 per plant; primary inflorescence 8.5 cm across and 1.5 cm tall, axillary flowers 6.5 cm across and 1.2 cm tall; comprising about 48 ray florets and about 700 disc florets; individual inflorescence head lasting about three weeks on or cut from plant.

Fragrance: Slightly musty with age.

Flowering period: Early summer (late June) to mid-summer in Michigan.

Peduncle: Strong, hispidulous, round to canaliculate but less canaliculate than stem, 6 to 20 cm long and 2.0 to 3.0 mm diameter at base.

*Peduncle color*.—Nearest RHS 137C.

Bud: Flattened capitate; with ray tepals still vertical, average about 22.0 mm across and 17.0 mm tall; adaxial and abaxial ray tepal coloration between RHS 155D and RHS 158D.

Ray florets: About 48 per inflorescence; arranged around perimeter of capitulum in two overlapping rows; 3.7 cm long and 8.0 mm wide, lanceolate, glabrous, acute apex normally two clefts producing center lobe about 1.0 mm long and 2.0 mm wide at base, and two others on either side about 1.0 mm long and 1.2 mm wide at base; base attenuate, margin entire, glabrous.

*Ray floret color*.—As tepals are first at 180° horizontal adaxial lighter than RHS 155D and abaxial lighter than RHS 155D; mature flower adaxial nearest RHS 155B and abaxial lighter than RHS 155D; base 10.0 mm on adaxial side and 12.0 mm on abaxial side nearest RHS 144B.

Disc florets: About 500 per inflorescence in center of capitulum, combined about 2.7 cm across and about 1.5 cm tall; individual floret about 8.0 mm tall and 1.2 mm wide, five tepals, about 3.0 mm long with acute apex, fused at base.

*Disc floret color*.—Tepal base between RHS 146 C and RHS 146B; apical 3 mm of tepals RHS 13A.

Androecium: Only in disc florets; five stamens fused together around style; about 4.0 mm long.

*Anther*.—Oblong; about 2.0 mm long and less than one mm wide, anther coloration nearest RHS 17A.

*Filaments*.—Fused together at apex, about 2.0 mm long and less than 0.1 mm diameter, filament coloration nearest RHS 2D.

*Pollen*.—Abundant; color between RHS N25B and RHS N25A.

Gynoecium: In ray florets and disc florets; single; about 7.0 mm long; Style about 5.0 mm long and less than 1 mm diameter, split and curved at apical 1.0 mm, style coloration nearest RHS 154D, stigma less than 0.5 mm diameter, with acute apex; stigma coloration between RHS 17D and RHS 17C; ovary about 2.0 mm long, color between RHS 147D and RHS 145D.

Receptacle: About 2.2 cm across and 7.0 mm tall; color nearest RHS 145D.

Involucre: Made of about three layers of phyllaries averaging 48 per head; to 3.0 across and 0.5 cm tall; glabrous abaxial and adaxial; entire margin, apex obtuse, base truncate.

Phyllaries: About 48 per head arranged in about three overlapping rows, 10 mm long and 2.2 mm wide; entire margin, apex obtuse, base truncate.

*Phyllaries color*.—Between RHS 144A and RHS 144B on abaxial and adaxial center portions, on margin; distal phyllaries with a 1.0 mm wide transparent margin in the apical 3.0 mm; proximal phyllaries with apical third nearest RHS 145A.

Fruit: Achene, pointed at base and rounded at distal end with longitudinal color striations nearest RHS N200A and lighter than RHS 155D; about 3 to 4 mm long and 1.5 mm across; about 200 seeds per head.

*Leucanthemum* 'Whoops-a-Daisy' grows best with adequate moisture but can tolerate some dryness once established. It is tolerant of high temperatures of at least 36° Celsius and cold hardy to at least USDA zone 5 as well as strong wind and rain. Other disease or pest resistance beyond that common to Shasta daisy has not been observed.

I claim:

1. The new and distinct Shasta daisy plant, *Leucanthemum* 'Whoops-a-Daisy' as herein shown and described useful for long-flowering attractive landscaping in borders, in mass, as accent plants, containerized for patio or indoor use, or as a cut flower.

* * * * *